United States Patent [19]

Nagano et al.

[11] 4,052,691
[45] Oct. 4, 1977

[54] HUMIDITY SENSOR

[75] Inventors: Kentaro Nagano; Koji Nomaki, both of Yokohama; Yukinori Kutsukake, Tokyo; Junji Nanao, Yokohama, all of Japan

[73] Assignee: Asahi Glass Company Ltd., Tokyo, Japan

[21] Appl. No.: 686,293

[22] Filed: May 14, 1976

[51] Int. Cl.$^2$ ............................................. H01L 7/00
[52] U.S. Cl. ................................ 338/35; 200/61.06; 219/522; 252/518; 252/519; 252/521
[58] Field of Search ............ 338/35, 34; 73/29, 336.5; 219/203, 522; 23/254 E; 340/235; 252/518, 519, 521; 200/61.06, 61.04

[56] References Cited

U.S. PATENT DOCUMENTS 2,806,991  9/1957  White .............................. 338/34 X
3,868,492  2/1975  Taylor ............................. 338/35 X Primary Examiner—C. L. Albritton
Attorney, Agent, or Firm—Oblon, Fisher, Spivak, McClelland & Maier

[57] ABSTRACT

A humidity sensor comprising a pair of spaced electrodes on an insulating substrate is formed by coating an orthophosphate as a sensitive membrane over at least a portion of the gap between the electrodes.

10 Claims, 3 Drawing Figures

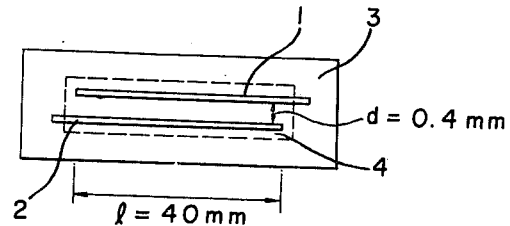
FIG. 1
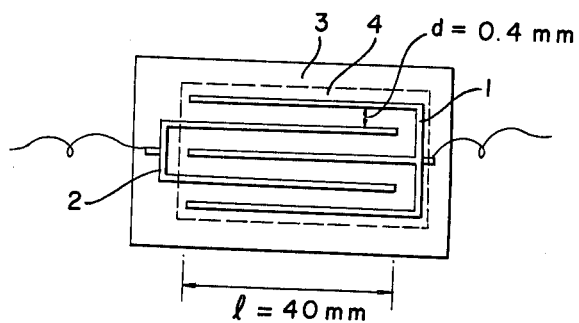
FIG. 2
FIG. 3 RESULTS OF LONG DRY-WET CYCLE TEST
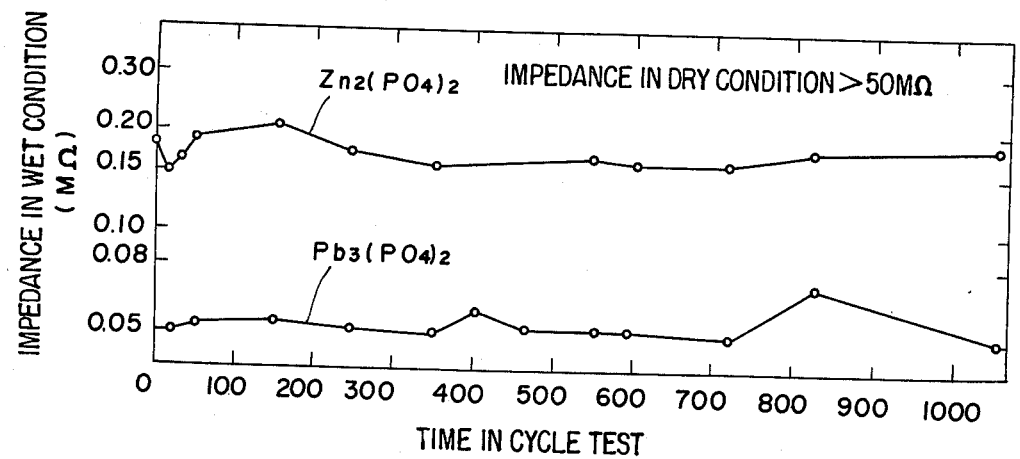

HUMIDITY SENSOR

BACKGROUND OF THE INVENTION

1. Field of the Invention

The present invention relates to an improved humidity sensor.

In order to maintain the transparency and good visibility characteristics of plate glass, glass plates have been provided with heating devices which prevent the accumulation of ice, frost, condensed moisture, etc. on the plates thereby permitting unimpaired vision through the glass plates. The heating devices normally are a conductive film or electric resistance strips located on the surface of the glass plate or between laminated glass plates. These glass plates have been used in automobiles, aeroplanes, ships, and other vehicles; in window glass plates for buildings or in other various apparatus and the like which should provide clear visibility under all weather conditions. Recently, an improved glass plate defogger has been developed which prevents cloudiness on glass surfaces by automatically heating the same only when fog forms on the surface of the glass plate. Such a defogging glass plate comprises a pair of electrodes disposed on the surface of a glass plate as a moisture detecting terminal. When moisture condenses between the pair of electrodes, a change of current or impedance between the electrodes caused by current is detected. When the changing current or impedance reaches a predetermined value, the electric heating element is activated thus providing heat to the glass plate. When the electrodes of the conventional humidity sensor for detecting condensed moisture are used, the impedance between the electrodes under the influence of condensed moisture varies depending upon the surface conditions of the glass plate between the electrodes, the atmosphere over the electrodes and lapses in time. It is difficult to prepare a humidity sensor for detecting condensed moisture which maintain the same impedance over long periods of time. For example, a humidity sensor comprising electrodes made of $RuO_2$ is chemically stable, but the impedance between the electrodes drifts upon ageing which adversely affects activation of the relay.

A need, therefore, continues to exist for an improved electrode sensing system for humidity sensors.

SUMMARY OF THE INVENTION

Accordingly, one object of the invention is to provide a humidity sensor system for detecting condensed moisture which has none of the abovementioned disadvantages and which exhibits stability of impedance characteristics with lapses of time, and which is durable over long periods of time.

Briefly, this object and other objects of the invention as hereinafter will become more readily apparent can be attained by coating an insulating substrate with an orthophosphate which is chemically stable and has substantial adhesiveness and which is characterized by the fact that small amounts of the orthophosphate dissolve as charge carriers in the condensed moisture so that the condensed moisture is electrically conducting. By this technique a desirable range of impedance is provided wherein an equilibrium state is maintained when moisture is condensed on the surface between the pair of electrodes which detects condensed moisture.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1 is a plane view of one embodiment of the humidity sensor of the invention;

FIG. 2 is a plane view of another embodiment of the humidity sensor of the invention; and FIG. 3 is a graph showing the relationship between impedance under wet conditions and the cycle test time as a result of a long dry-wet cycle test.

DETAILED DESCRIPTION OF THE PREFERRED EMBODIMENTS

The object of the present invention is to provide a humidity sensor for detecting condensed moisture. The sensor comprises a pair of electrodes disposed on an insulating substrate and an orthophosphate membrane coated partially or wholly between the pair of the electrodes. The pair of electrodes formed on the insulating substrate are made of a conductive material having a high chemical resistance including conductive metal oxides such as $RuO_2$, $In_2O_3$, $SnO_2$, $V_2O_5$, $Tl_2O_3$ and the like, and conductive metals which do not easily migrate such as Au, Pd, Pt, Al and the like The conductive metal oxide or the conductive metal is admixed and kneaded with a glass frit, a vehicle, a binder and other additives, and the resulting paste is printed onto an insulating substrate by screen-printing or some other printing method in the form of a pair of electrodes in any desired pattern. The printed composition is dried and sintered to form the electrodes which detect condensed moisture.

It is also possible to form the electrodes from a conductive metal or a conductive metal oxide by various coating methods such as by vacuum deposition, by a spatter method, by the CLD method or the like. The preferred pattern of the humidity sensor which detects condensed moisture has the electrodes separated by a desirable gap over which gap the change in impedance between the electrodes resulting from the condensed moisture on the surface of the insulating substrate is detected. The size of the gap ranges from 0.1 to 10.0 mm.

Each pair of electrodes can have few to ten or more branches each of which are alternately faced. In the invention, an orthophosphate is coated between the pair of electrodes. When moisture condenses in the gap between the electrodes, the orthophosphate dissolves in only very small amounts in the condensed moisture to act as charge carriers, whereby an equilibrium state is maintained. For example, one of the suitable orthophosphates of the invention, i.e. zinc orthophosphate, dissociates as follows releasing $Zn^{++}$ ions and $PO_4^{---}$ ions as charge carriers.

$$Zn_3(PO_4)_2 \rightleftarrows 3Zn^{++} + 2PO_4^{---}$$

The orthophosphate is chemically stable and does not decompose in the preparation of the coated membrane. Moreover, the formability of the coated membrane is excellent. These characteristics make the orthophosphates quite suitable for forming the sensitive zone of the humidity sensors. The orthophosphate glazes when the membrane of the orthophosphate is formed at high temperature, and forms a stable durable membrane.

Preferably, an orthophosphate is selected which maintains a constant impedance for a long time in a constant ion concentration without a significant consumption of ions. That is, the orthophosphate has a solubility in water of less than 0.1 g/100 gH$_2$O which represents a relatively low solubility of the orthophosphate in water. Suitable orthophosphates include the following:

| Compound | Solubility (g/100 g H$_2$O at room temperature) |
|---|---|
| Zn$_3$(PO$_4$)$_2$ | $<1 \times 10^{-6}$ |
| Pb$_3$(PO$_4$)$_2$ | $1.4 \times 10^{-5}$ |
| Li$_3$PO$_4$ | $3.4 \times 10^{-2}$ |
| Mn$_3$(PO$_4$)$_2$ | $<1 \times 10^{-5}$ |
| Ca$_3$(PO$_4$)$_2$ | $2.5 \times 10^{-3}$ |
| Mg$_3$(PO$_4$)$_2$ | $2 \times 10^{-2}$ |
| Fe$_3$(PO$_4$)$_2$ | $<1 \times 10^{-6}$ |

Preferably zinc orthophosphate is used because its solubility is very low which results in a very small loss of ions while having the ability to maintain a constant impedance for a long time. The orthophosphate is coated on a substrate as a membrane having a thickness of 10 to 500$\mu$, preferably 50 to 100$\mu$, in a manner such that the membrane at least partially covers the area between the facing electrodes.

The methods by which the orthophosphate can be coated include a plasma flame spraying method, a sintering method, a vacuum deposition method, a spattering method and the like. Preferably, the membrane is formed at high temperature such as in a plasma flame spraying method or a sintering method because the orthophosphate is deposited in a glazed form. The orthophosphate coating between both of the electrodes can be of a single orthophosphate or a mixture of orthophosphates. It is also possible to form a membrane by blending an orthophosphate with another membrane forming component.

Suitable insulating substrates used in the invention include glass plates, alumina plates, crystallized glass plates and the like, or a heat-resisting plastic plate. When a glass plate is used, it is preferable to use a glass plate having a low alkali content or no alkali content which minimizes interference by alkali metal ions which may dissolve into the condensed moisture.

Referring to the drawings, certain embodiments of the humidity sensor will be illustrated. In FIGS. 1 and 2, reference numeral 1 designates embodiments of the anode, and 2 designates embodiments of the cathode. Anode 1 and the cathode 2 face each other and are formed on an insulating substrate 3. The gap $d$ between both of the electrodes is preferably 0.1 to 3 mm, (it is 0.4 mm in the drawings). The length ($l$) of each electrode is preferably 1 to 100 cm (it is 4 cm in the drawings). The width of each strip of the electrode is preferably 0.4 to 3 mm (it is 1 mm in the drawings). The orthophosphate membrane 4 is deposited between the anode 1 and the cathode 2.

Having generally described the invention, a more complete understanding can be obtained by reference to certain specific examples, which are provided herein for purposes of illustration only and are not intended to be limiting unless otherwise specified.

EXAMPLE

A conductive composition prepared by admixing and kneading 100 parts by wt. of RuO$_2$ powder, 61 parts by wt. of glass frit powder and 16 parts by wt. of a vehicle was printed on a glass plate by a screen printing method in the pattern shown in FIG. 2. The printed glass plate was heated at about 650° C to sinter the conductive composition to form a glass plate having four electrodes. Thereafter, a powder of Zn$_3$(PO$_4$)$_2$, Pb$_3$(PO$_4$)$_2$, Fe$_3$(PO$_4$)$_2$ or Mg$_3$(PO$_4$)$_2$ was coated by plasma flame spraying on a glass substrate having a pair of electrodes so as to form a membrane having a thickness of 50 to 100$\mu$ as shown in FIG. 2. The results of several long dry-wet cycle tests concerning the variation of impedance under wet conditions versus cycle time for the humidity sensors using Zn$_3$(PO$_4$)$_2$ or Pb$_3$(PO$_4$)$_2$ are shown in FIG. 3. The results of the water resistance test, surface contamination resistance test, ageing test and solvent resistance test for each of the samples are presented in Table 1.

LONG DRY-WET CYCLE TEST

Each humidity sensor was formed on a defogging glass plate prepared by the printing of electric heating element strips. The defogging glass plate having the humidity sensor was disposed on one wall of an airtight chamber. Cold water was sprayed onto the outer surface of the glass plate to cool the outer surface, whereby condensed moisture was formed on the inner surface of the glass plate, thus setting up the wet condition for the testing of the humidity sensor. When the impedance of the humidity sensor reached 0.5 M$\Omega$ in wet conditions, the spray of water was stopped by command of a controller, and the current was passed through the electric heating element to heat the surface of the glass plate resulting in defogging of the glass plate and thereby presenting the dry condition of the humidity sensor. When the impedance of the humidity sensor increased to 1 M$\Omega$, the current passing through the electric heating element broke down to start the spray of water again. The wet-dry-wet cycle was repeated and the impedance was measured by a tester.

Table 1

(Variation of impedance under wet condition)

| Test Item | Sample | | | |
|---|---|---|---|---|
| | Zn$_3$(PO$_4$)$_2$ | Pb$_3$(O$_4$)$_2$ | Fe$_3$(PO$_4$) | Mg$_3$(PO$_4$)$_2$ |
| Water resistance test: | no change | no change | no change | no change |
| Condition (a) | >12 hours | >10 hours | >12 hours | >8 hours |
| Condition (b) | >4 hours | >4 hours | >4 hours | >2 hours |
| Surface contamination resistance test: | | | | |
| Condition (c) | slightly sensitized | slightly sensitized | slightly sensitized | no change sensitized |
| Condition (d) | slight change | slight change | slight change | no change |
| Condition (e) | no change | no change | no change | no change |
| Solvent resistance test: | | | | |
| Petroleum benzine | no change | no change | no change | no change |
| Trichloroethylene | no change | no change | no change | no change |
| Ethyl alcohol | slight | slight | slight | slight |

Table 1-continued

| Test Item | (Variation of impedance under wet condition) Sample | | | |
|---|---|---|---|---|
| | $Zn_3(PO_4)_2$ | $Pb_3(PO_4)_2$ | $Fe_3(PO_4)$ | $Mg_3(PO_4)_2$ |
| | change, recovered | change, recovered | change, recovered | change, recovered |
| Aging test: | | | | |
| 1) Room | no change | no change | no change | no change |
| 2) Dried chamber (R.H. 1%) | slight change for 50 days, recovered in room | slight change for 40 days, recovered in room | slight change for 50 days, recovered in room | slight change for 50 days, recovered in room |
| 3) Humidified chamber (R.H. 95%) | slight change for 10 days, recovered in room | slight change for 5 days, recovered in room | slight change for 10 days, recovered in room | slight change for 5 days, recovered in room |

In the technique of the invention, moisture condenses on a portion of the electrodes whereby the orthophosphate coated between the electrodes dissociate to form ions which act as charge carriers thereby imparting conductivity to the deposited moisture. The amount of orthophosphate which dissolves in water is quite small, and the equilibrium is maintained whereby a constant impedance can be given. The orthophosphate is dissolved in water to form ions which act as ion carriers moving between the electrodes. When the sensor returns to the dry condition, the ions revert to the orthophosphate. As a result, the loss of orthophosphate is very low and the increase of impedance which normally accompanies conventional electrodes which experience lapses of time for long time periods is low which maintains the impedance of the electrodes within a desirable range. As shown in Example, the variation of impedance is quite small in the dry-wet cycle test. The humidity sensor is especially useful as a sensor for detecting condensed moisture on a defogging glass plate.

Having now fully described the invention, it will be apparent to one or ordinary skill in the art that many changes and modifications can be made thereto without departing from the spirit or scope of the invention as set forth herein.

We claim:

1. A humidity sensor for detecting condensed moisture, which comprises:
    a pair of spaced electrodes disposed on an insulating substrate;
    and a moisture sensitive membrane of an orthophosphate which at least partially covers the gap between said electrodes.

2. The humidity sensor according to claim 1, wherein the orthophosphate is selected from the group consisting of orthophosphates of zinc, lead, lithium, manganese, calcium, magnesium, iron and mixtures thereof.

3. The humidity sensor according to claim 1, wherein the orthophosphate is zinc orthophosphate.

4. The humidity sensor according to claim 1, wherein the membrane of the orthophosphate has a thickness of 10 to 500μ.

5. The humidity sensor according to claim 1, wherein the orthophosphate is coated on said insulating substrate by a plasma flame spraying method.

6. The humidity sensor according to claim 1, wherein the orthophosphate is coated on said insulating substrate and heated at high temperature.

7. The humidity sensor according to claim 1, wherein the orthophosphate is coated on said insulating substrate by a sintering method.

8. The humidity sensor according to claim 1, wherein the orthophosphate is coated on said insulating substrate by a vacuum deposition method.

9. The humidity sensor according to claim 1, wherein the orthophosphate is coated on said insulating substrate by a spattering method.

10. A defogging glass plate, which comprises:
    an insulating substrate deposited on a glass plate to be defogged;
    a humidity sensor on said insulating substrate which comprises a pair of spaced electrodes with a moisture sensitive membrane of an orthophosphate at least partially covering the gap between said spaced electrodes; and
    an electric heating element connected to said humidity sensor, such that activation of said electric heating element is controlled by variation of the impedance between said electrodes.

* * * * *

UNITED STATES PATENT AND TRADEMARK OFFICE
CERTIFICATE OF CORRECTION

PATENT NO. : 4,052,691
DATED : October 4, 1977
INVENTOR(S) : Nagano et al

It is certified that error appears in the above-identified patent and that said Letters Patent are hereby corrected as shown below:

Please insert the following:

--[30] Foreign Application Priority Data

June 20, 1975 Japan .....................50-74365--

Signed and Sealed this

Fourth Day of April 1978

[SEAL]

Attest:

RUTH C. MASON
Attesting Officer

LUTRELLE F. PARKER
Acting Commissioner of Patents and Trademarks